US008282366B2

(12) United States Patent
Hilber et al.

(10) Patent No.: US 8,282,366 B2
(45) Date of Patent: Oct. 9, 2012

(54) MICROPUMP

(75) Inventors: Josef Hilber, Allenwinden (CH); Sigfrid Straessler, St-Saphorin-sur-Morges (CH)

(73) Assignee: Sensile Pat AG, Baar (CH)

(*) Notice: Subject to any disclaimer, the term of this patent is extended or adjusted under 35 U.S.C. 154(b) by 1138 days.

(21) Appl. No.: 12/086,661

(22) PCT Filed: Dec. 8, 2006

(86) PCT No.: PCT/IB2006/003596
§ 371 (c)(1),
(2), (4) Date: Jun. 17, 2008

(87) PCT Pub. No.: WO2007/074363
PCT Pub. Date: Jul. 5, 2007

(65) Prior Publication Data
US 2009/0123309 A1    May 14, 2009

(30) Foreign Application Priority Data

Dec. 28, 2005  (EP) .................................. 05405726
Nov. 2, 2006  (EP) .................................. 06405462

(51) Int. Cl.
*F04B 17/00*  (2006.01)
(52) U.S. Cl. ....................................................... 417/420
(58) Field of Classification Search .............. 417/53, 417/420, 465; 415/172.1
See application file for complete search history.

(56) References Cited

U.S. PATENT DOCUMENTS

| 3,459,337 | A | * | 8/1969 | Williamson | .................. 222/183 |
| 4,152,098 | A | | 5/1979 | Moody et al. | |
| 4,734,092 | A | | 3/1988 | Millerd | |
| 4,883,467 | A | | 11/1989 | Franetzki et al. | |
| 4,964,533 | A | | 10/1990 | Allington et al. | |
| 6,506,033 | B2 | * | 1/2003 | Fukami | ........................ 417/420 |
| 2001/0043864 | A1 | | 11/2001 | Maruyama et al. | |
| 2004/0101426 | A1 | * | 5/2004 | Wahlberg | ...................... 417/492 |
| 2005/0182389 | A1 | * | 8/2005 | LaPorte et al. | ............. 604/890.1 |
| 2007/0071596 | A1 | | 3/2007 | Ryser et al. | |

FOREIGN PATENT DOCUMENTS

| CH | 688 224 A | 6/1997 |
| EP | 1 160 450 A | 12/2001 |
| WO | WO 93/20864 A | 10/1993 |
| WO | WO 2005/039673 A | 5/2005 |
| WO | WO 2005/039674 A1 | 5/2005 |

OTHER PUBLICATIONS

International Search Report for PCT/IB2006/003596 issued by the European Patent Office on Jul. 10, 2007.

* cited by examiner

*Primary Examiner* — Devon Kramer
*Assistant Examiner* — Amene Bayou
(74) *Attorney, Agent, or Firm* — Saliwanchik, Lloyd & Eisenschenk

(57) ABSTRACT

A pump including a stator, a rotor comprising an axial extension slidably and rotatably mounted at least partially in a rotor chamber of the stator, and at least first and second valves between an inlet and the rotor chamber, respectively between the rotor chamber and an outlet, that open and close as, a function of at least the angular displacement of the rotor. The pump comprises interacting cam elements on the rotor and stator and biasing elements acting on the rotor for applying a force on the rotor in the axial direction of the stator cam elements.

37 Claims, 16 Drawing Sheets

FIG. 5
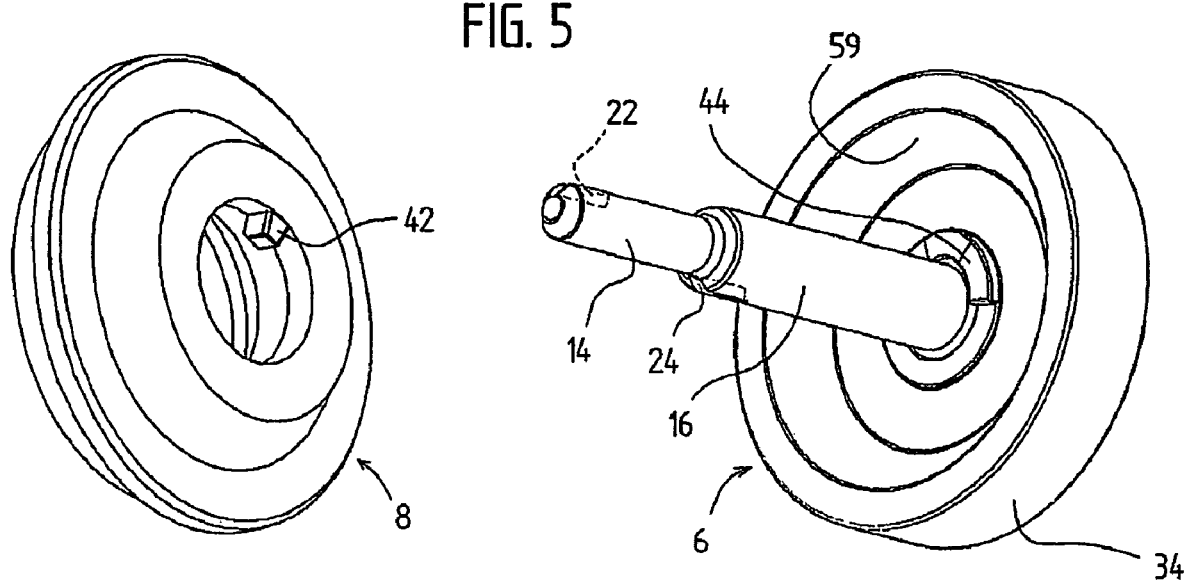
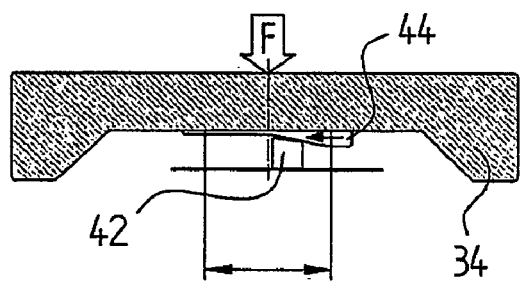
FIG. 6a
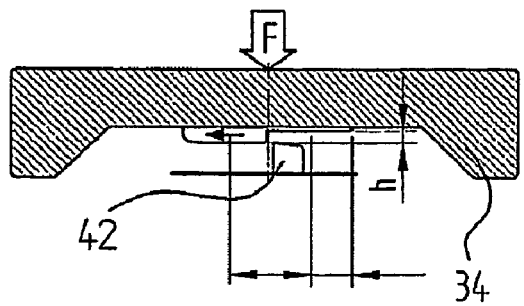
FIG. 6b
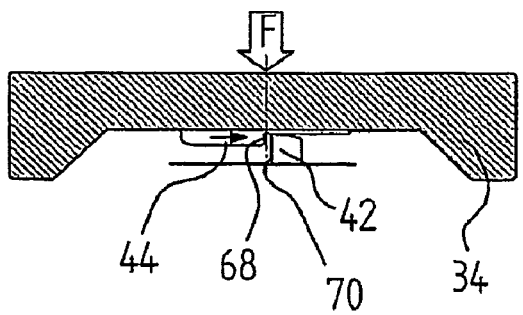
FIG. 6c

FIG. 7
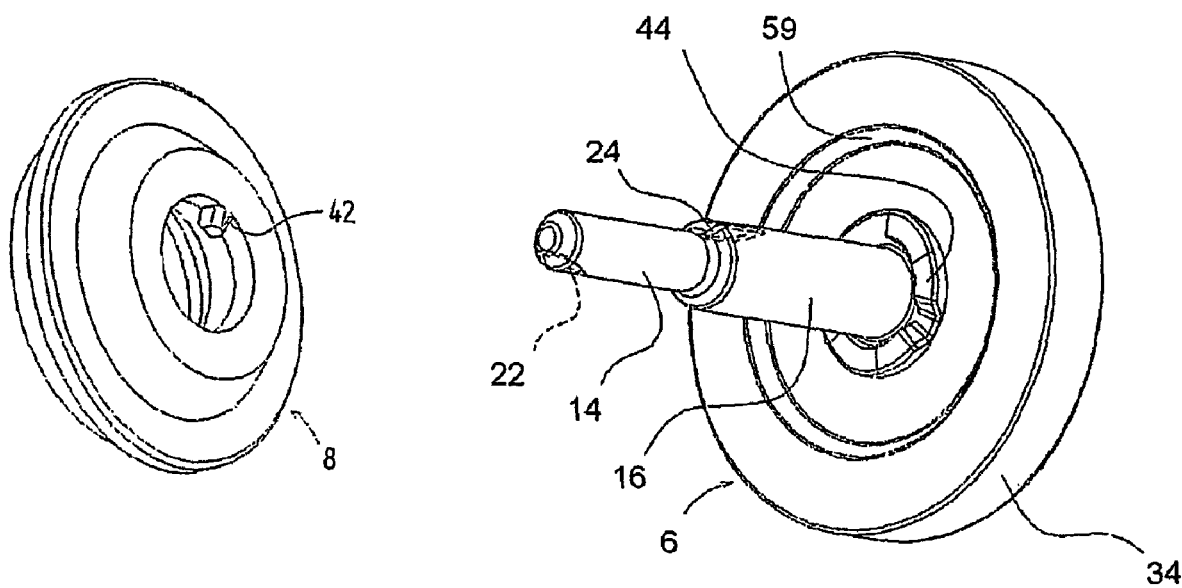
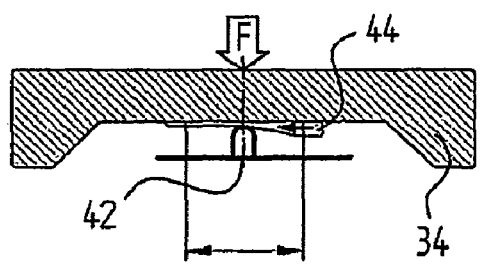
FIG. 8a
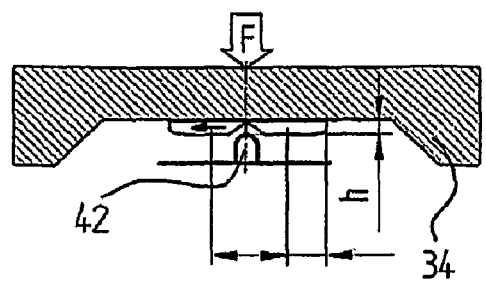
FIG. 8b

MICROPUMP

CROSS-REFERENCE TO RELATED APPLICATION

This application is the U.S. national stage application of International Patent Application No. PCT/IB2006/003596, filed Dec. 8, 2006, the disclosure of which is hereby incorporated by reference in its entirety, including all figures, tables and amino acid or nucleic acid sequences.

The present invention relates to a micropump system, in particular a micropump system for medical applications.

A micropump that is well adapted for precise subcutaneous administration of small quantities of a liquid drug, such as insulin, is described in international application WO 2005 039674. The aforementioned micropump is precise, compact, portable, and reliable because of the simplicity of its construction and its particular functioning principle. Nevertheless, the subcutaneous delivery of liquid drugs requires a high level of safety, some of the important requirements being to ensure that no air is injected into the patient's blood system and to ensure that the amount of drug actually injected corresponds to the reading of the pump control unit.

There is also a need to reduce the number and complexity of operations that need to be effected by a user for operation of the drug delivery system, such as interconnection of components, for example reservoir cartridges to a pump, in order to reduce the risk of false manipulations by the user.

There is moreover a continuous need to reduce the cost of medical devices.

In view of the aforegoing, an object of this invention is to provide a pump for medical applications that is accurate, reliable, compact, and very safe to use.

It would be advantageous to provide a micropump that is particularly cost effective to manufacture, such that it could be provided as a disposable system.

It would be advantageous to provide a cost effective disposable liquid drug delivery micropump that may be easily integrated with a reservoir comprising the drug to be delivered and disposed of with the drug reservoir, when empty.

Objects of this invention have been achieved by providing a pump according to claim 1.

Disclosed herein is a pump, in particular adapted for medical applications, including a stator, a rotor comprising an axial extension slidably and rotatably mounted at least partially in a rotor chamber of the stator adapted to effect a pumping action, and at least first and second valves between an inlet and the rotor chamber, respectively between the rotor chamber and an outlet portion of the pump. The valves open and close as a function of at least the angular displacement of the rotor. The pump further comprises interacting cam elements on the rotor and stator and biasing means acting on the rotor for applying a force on the rotor in the axial direction of the stator cam element.

In a preferred embodiment, the rotor comprises first and second axial extensions of different diameters with liquid supply channels, and sealing rings fixed to the housing being mounted around the first and second axial extensions, to form therebetween first and second valves. The sealing rings are arranged generally at an oblique angle with respect to a plane perpendicular to the axis of rotation of the rotor, such that when the rotor turns, the extremity of each liquid supply channel passes from one side of the sealing ring to the other side, thereby opening and closing liquid communication across the sealing ring. Over a 360° rotation cycle of the rotor, the rotor also effects an axial displacement when either valve is open, thus generating a pumping action due to the change in volume resulting from the difference in diameter between the two axial extensions of the rotor. The functioning principle of the latter embodiment is similar to the functioning principle of the micropump described in WO 2005 039674 the contents of which are incorporated herein by reference.

In the invention, the axial displacement of the rotor is generated by a cam surface of a cam element on the rotor, cooperating with a complementary cam surface of a complementary cam element on the stator housing, and means for applying an axial force pushing the rotor towards a face of the stator.

The axial force on the rotor may be generated by a spring pressing on the rotor, or by a magnet. In the preferred embodiment, a spring is provided in view of its simplicity, the spring comprising a central protrusion that presses against the rotor at the axial center thereof in order to minimize frictional forces therebetween.

The liquid supply channels are positioned with respect to the sealing rings, such that over a certain angle in the transition from the open position of one valve to the open position of the other valve, both valves are closed. This ensures that, taking into account any manufacturing tolerances, both valves are never simultaneously open in order to avoid a free flow path between the liquid reservoir and the subcutaneous needle.

In at least one of the angular zones in which both valves are closed, the camming surfaces are not in contact with each other and the cam element on the rotor is at a certain axial distance from the stator. In the event that there is an unintended leak in one of the sealing rings, or if there is air within the liquid chamber of the pump system, an axial force exerted between the rotor and stator will cause the relative displacement of the rotor with respect to the stator. The axial displacement of the rotor may be detected by a sensor, for example a Hall sensor or any other known position sensor, thereby signaling a malfunction to the control unit of the pump.

The cam elements may also be used to determine a reference position of the rotor relative to the stator, by advancing the rotor and then reversing the direction until the cam elements abut. The reference position may be used to set the start position of the rotor in order to determine the angular position of the rotor and in particular the cam element thereon relative to the stator in order to accurately determine the stop position.

The rotor may be made of an injected plastic material with permanent magnets embedded therein, driven by stator coils on a drive module that may be inserted over an end of the pump module.

Objects of the invention have also been achieved by providing a pump module according to claim 11.

Disclosed herein is a pump module including a rotor comprising first and second axial extensions having different diameters, a stator comprising a stator housing having a rotor chamber for receiving at least a portion of the axial extensions therein, and first and second seals mounted around the first and second axial extensions. The axial extensions are provided with liquid supply channels cooperating with the respective first and second seals to create first and second valves that open and close liquid communication across the respective seal as a function of the angular displacement of the rotor. The pump module comprises a third sealing ring fixed to the stator housing and positioned around the first large diameter axial extension, proximate the rotor body, to delimit the outlet portion of the rotor chamber positioned between the second and third sealing rings.

With this arrangement, the rotor body is sealed off from the liquid being pumped and the volume of liquid within the pump is kept to a minimum, thereby facilitating the evacuation of any air therein during the start cycle of the pump. Moreover, unnecessary shear of the liquid by the rotor body is avoided, thus reducing possible deterioration of sensitive or large molecules due to shear effect. This configuration also eliminates any backflow pumping during the pump cycle, in other words, provides forward flow pumping only.

The various sealing rings may advantageously be integrally molded with plastic housing parts to form a particularly a compact and cost effective pump arrangement.

Objects of the invention have also been achieved by providing a method of operating a pump module as set forth in claim 17.

Disclosed herein is a method of operating a pump including a stator, a rotor comprising an axial extension slidably and rotatably mounted at least partially in a rotor chamber of the stator, and at least first and second valves between an inlet and the rotor chamber, respectively between the rotor chamber and an outlet portion, that open and close as a function of at least the angular to displacement of the rotor, the method including detecting axial displacement of the rotor as a function of the angular position of the rotor and comparing the axial displacement detected with an expected displacement value in order to determine if there is a malfunction. The malfunction may be due to blockage in the downstream section of the pump or in elements or devices connected to the pump outlet, or due to leakage of a valve, or air in the rotor chamber.

In a preferred embodiment, first and second seals are mounted around first and second axial extensions of the rotor which are provided with liquid supply channels cooperating with the respective first and second seals in order to create the first and second valves that open and close liquid communication across the respective seal as a function of at least the angular displacement of the rotor. The valves could however be configured differently without departing from the scope of the invention, for example the valves could be built into the stator and bridge across seals between the stator and rotor that delimit the rotor chamber.

The above described testing method advantageously allows detection of a faulty valve or the presence of air in the rotor chamber, or blockage downstream of the rotor chamber, for example due to an occlusion in the outlet section or catheter. The aforementioned method can be employed in pumps with the structural features set forth in the present invention or more generally in the prior art pumps having the structural features described in WO 2005039674, or even other pump configurations where the pumping action is based on combined rotational and axial displacement of the rotor in a rotor chamber Also disclosed herein is a method of operating a pump module including a rotor comprising an axial extension, a stator comprising a stator housing having a rotor chamber receiving at least a portion of the axial extension therein, and at least first and second valves between an inlet and the rotor chamber, respectively between the rotor chamber and an outlet portion, that open and close as a function of at least the angular displacement of the rotor, the pump module further comprising interacting cam elements on the rotor and stator and biasing means acting on the rotor for applying a force on the rotor in the axial direction of the stator cam element, the method including:
  turning the rotor one or more cycles in a pumping direction; and
  subsequently reversing the rotor rotation until shoulders of the rotor and stator cam elements abut in order to define a reference angular position of the rotor relative to the stator.

The reference angular position may advantageously be used to accurately determine and find the test position when performing a valve test procedure, or to ensure that the rotor is stopped in a position where the valves are both closed when operation of the pump is stopped during use.

Also disclosed herein is a patch pump device comprising a disposable unit including a pump module mounted to a reservoir, and a base unit comprising a drive for driving the rotor of the pump module. The disposable unit of the patch pump device may further comprise a catheter adapted for subcutaneous drug delivery, connected to an outlet of the pump module.

Further objects and advantageous aspects of the invention will be apparent from the claims and the following detailed description of an embodiment of the invention in conjunction with the drawings in which:

FIG. 1b is a perspective partial cross-sectional view of the pump system shown in FIG. 1a;

Figure 1A:
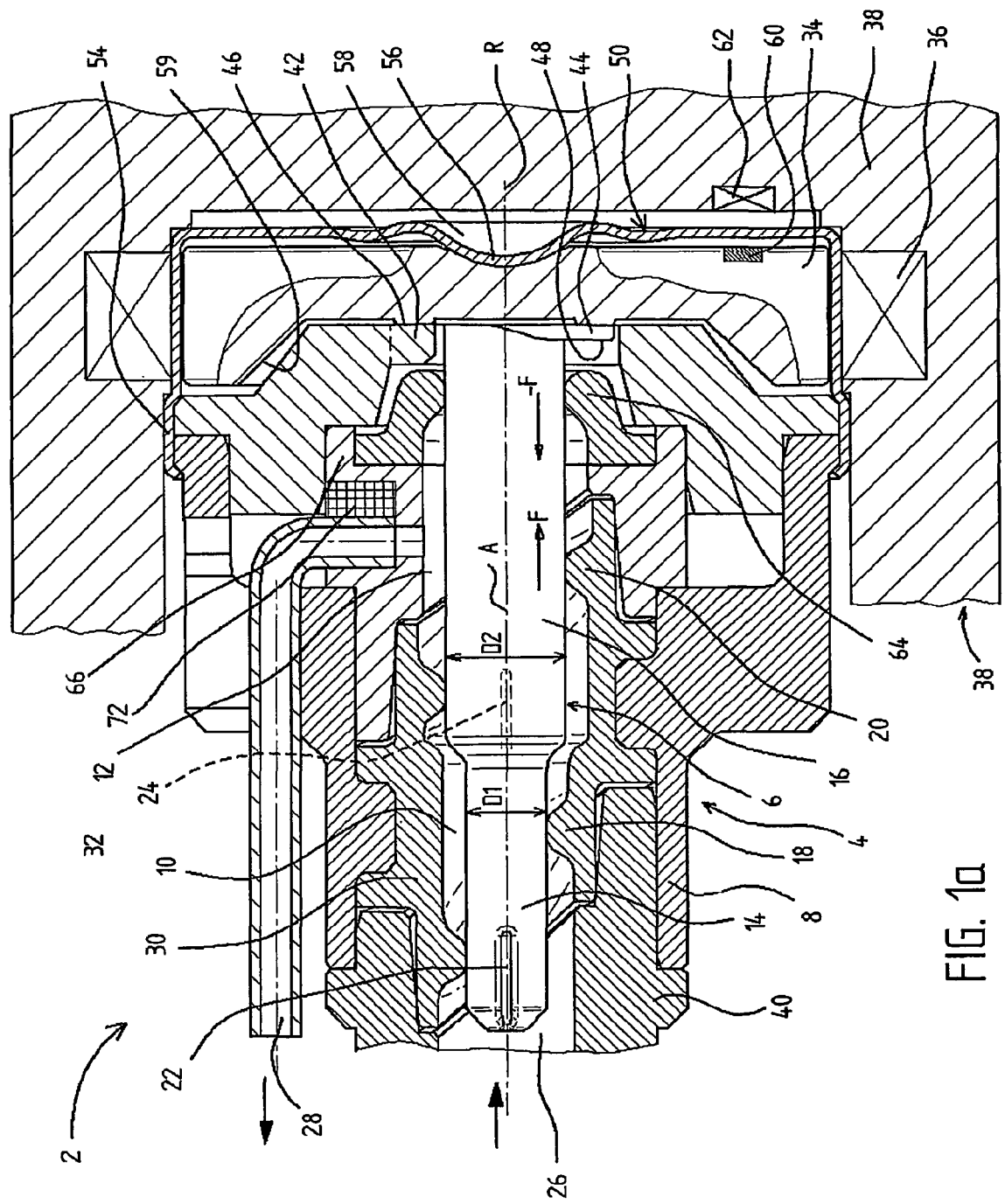
FIG. 1a is a cross-sectional view of a pump system according to an embodiment of this invention, whereby the rotor is at an initial angular position identified herein as 0°.
Figure 1B:
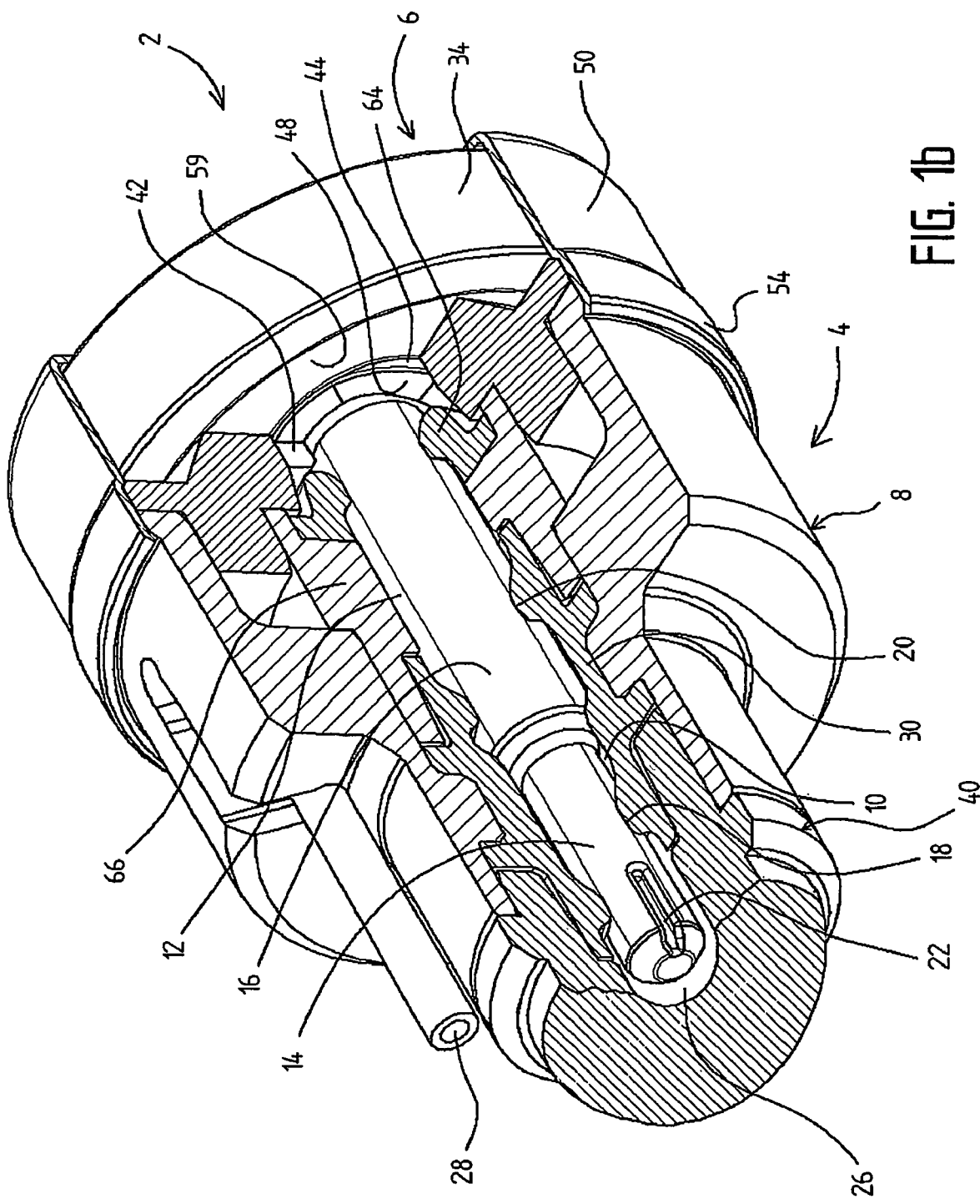
Figure 2A:
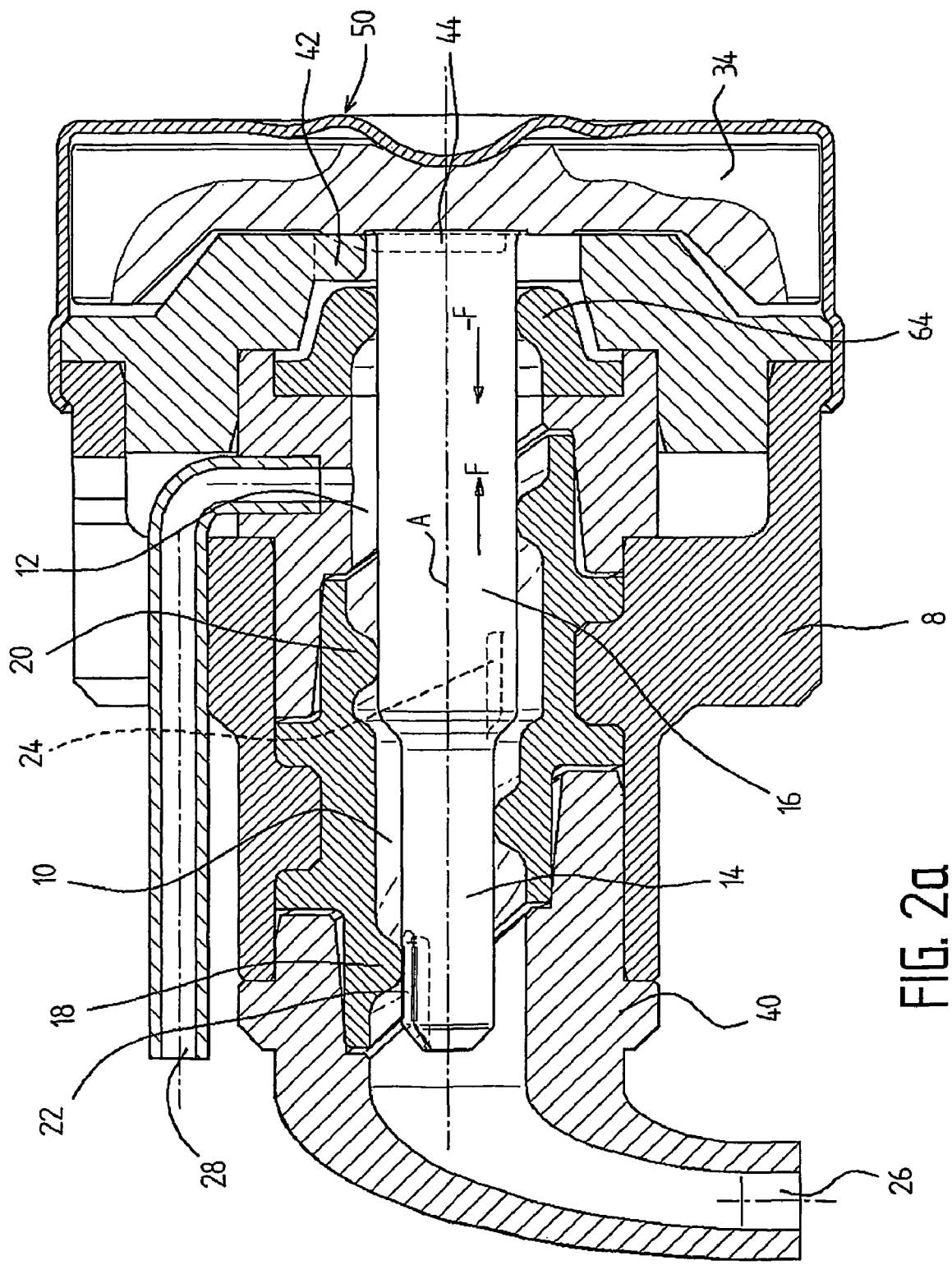
FIGS. 2a and 2b are similar to FIGS. 1a and 1b, respectively, except that the rotor is in an angular position of 60°.
Figure 2B:
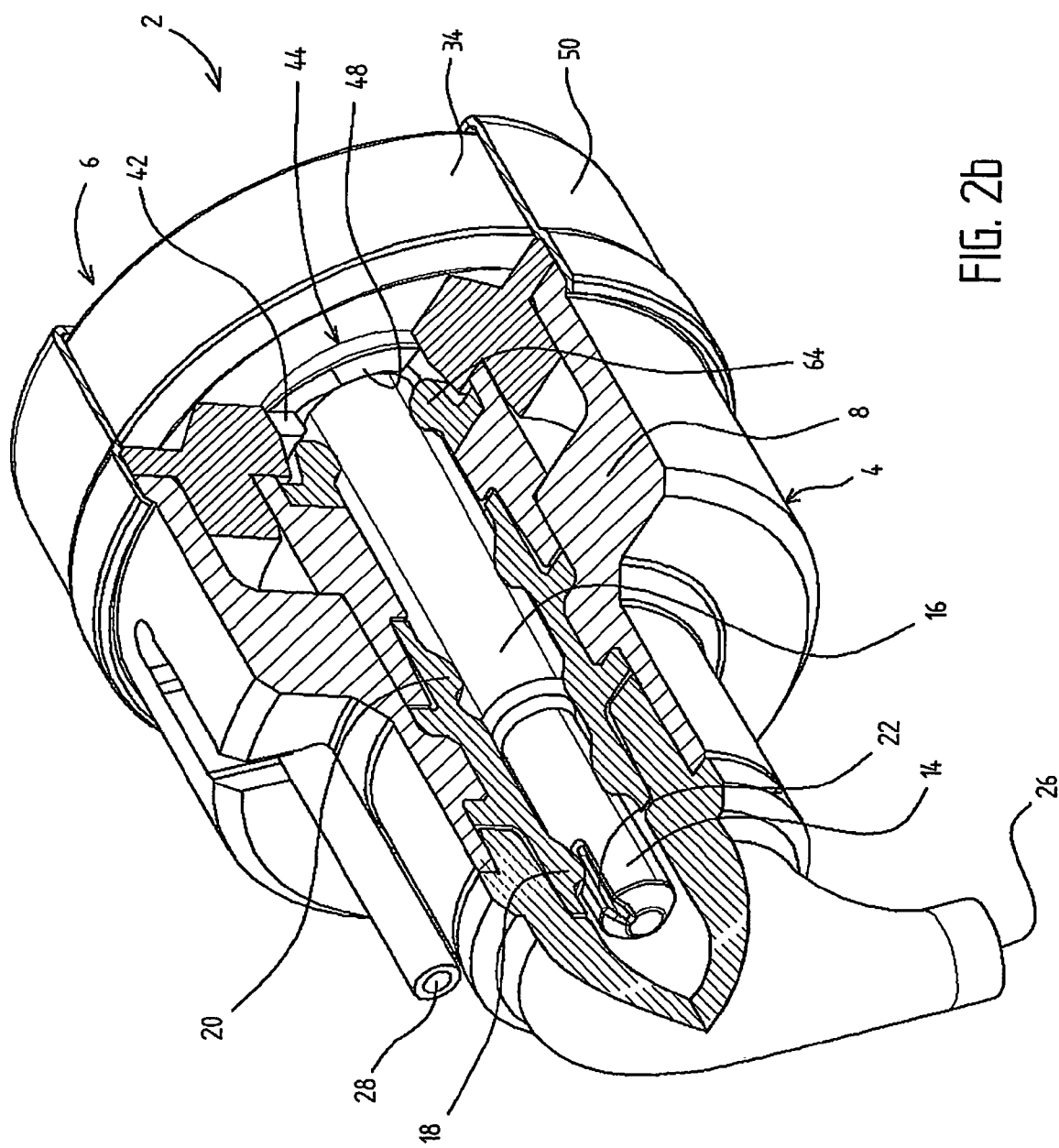
Figure 3A:
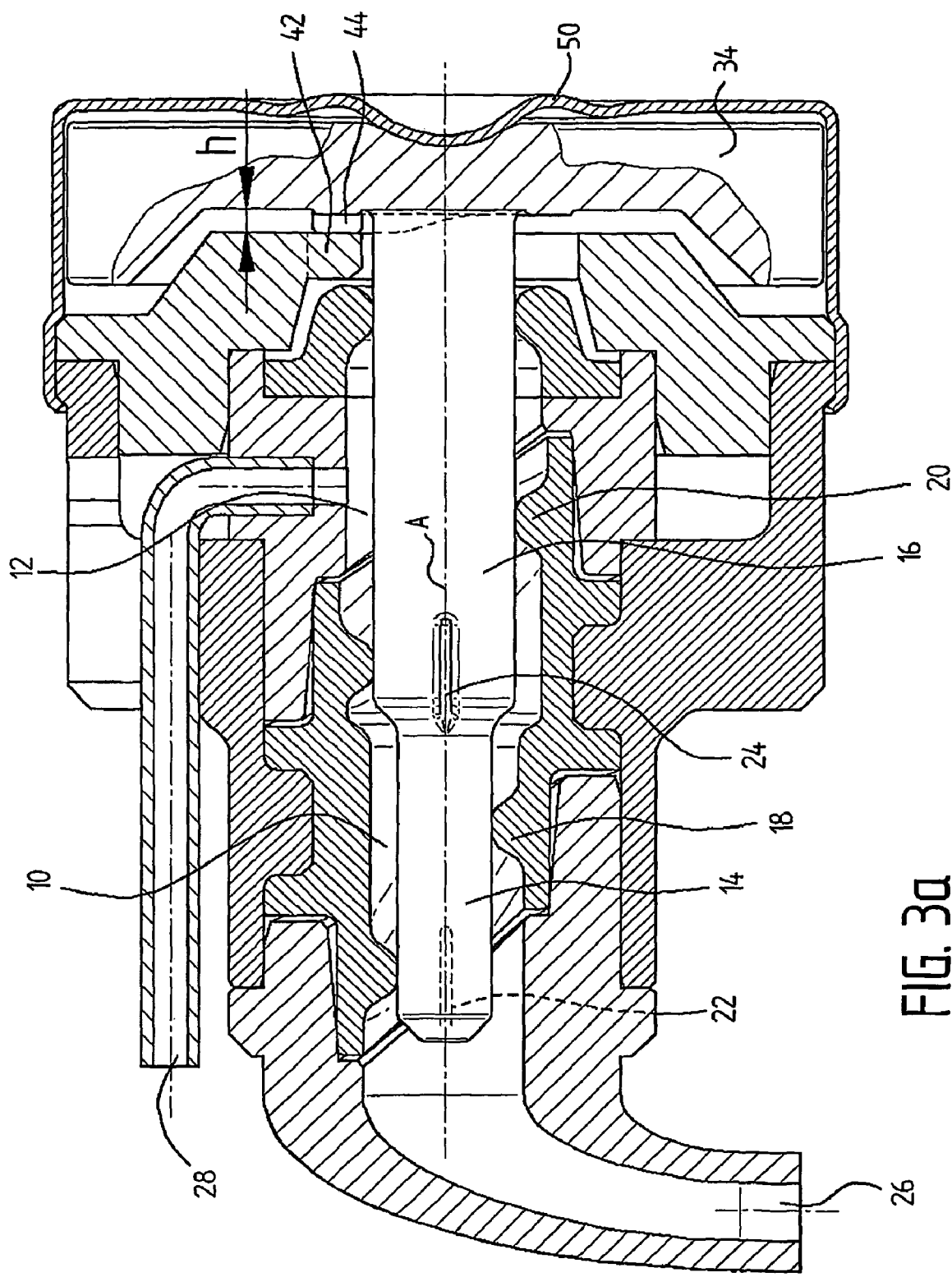
Figure 3B:
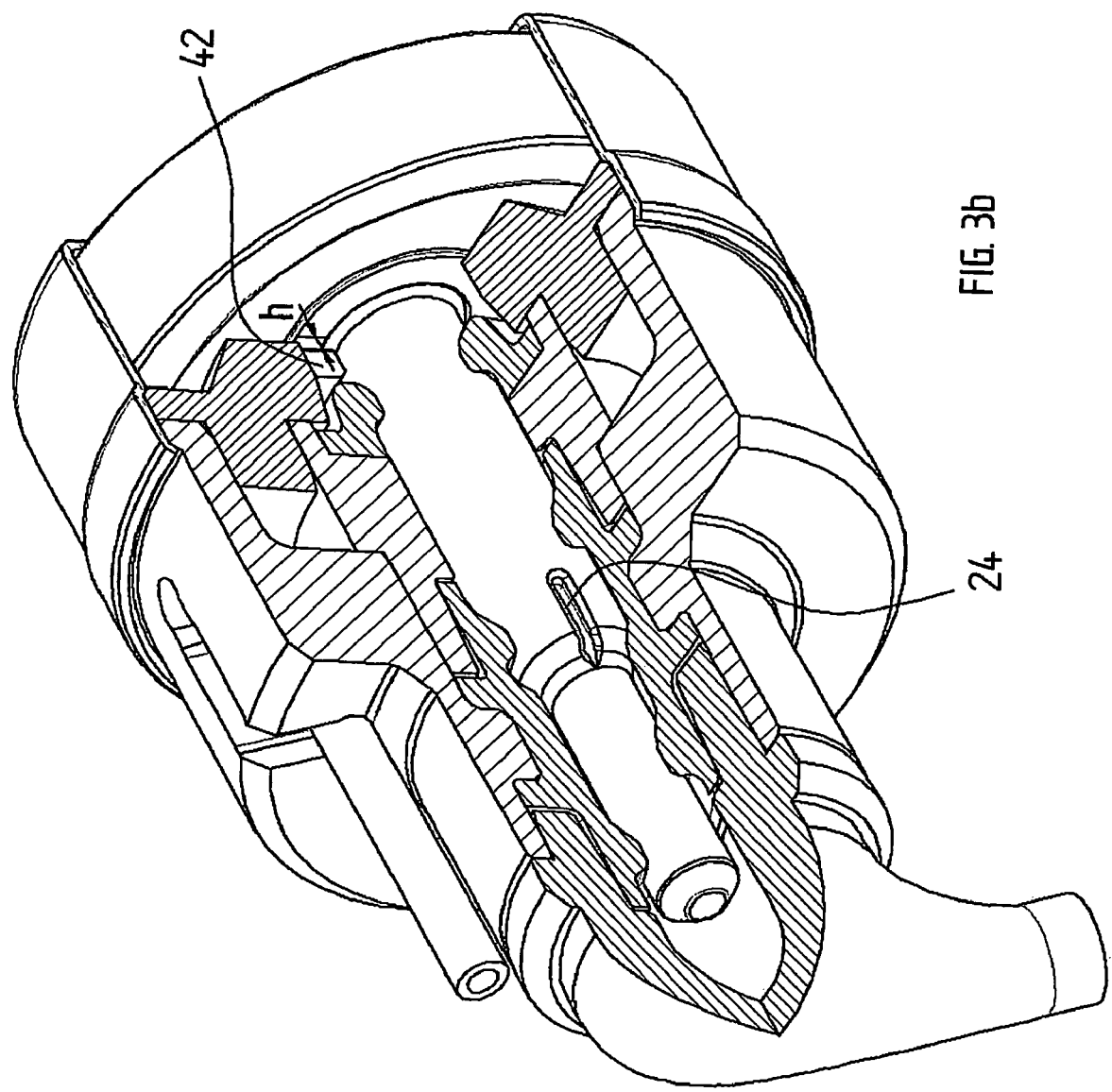
Figure 3C:
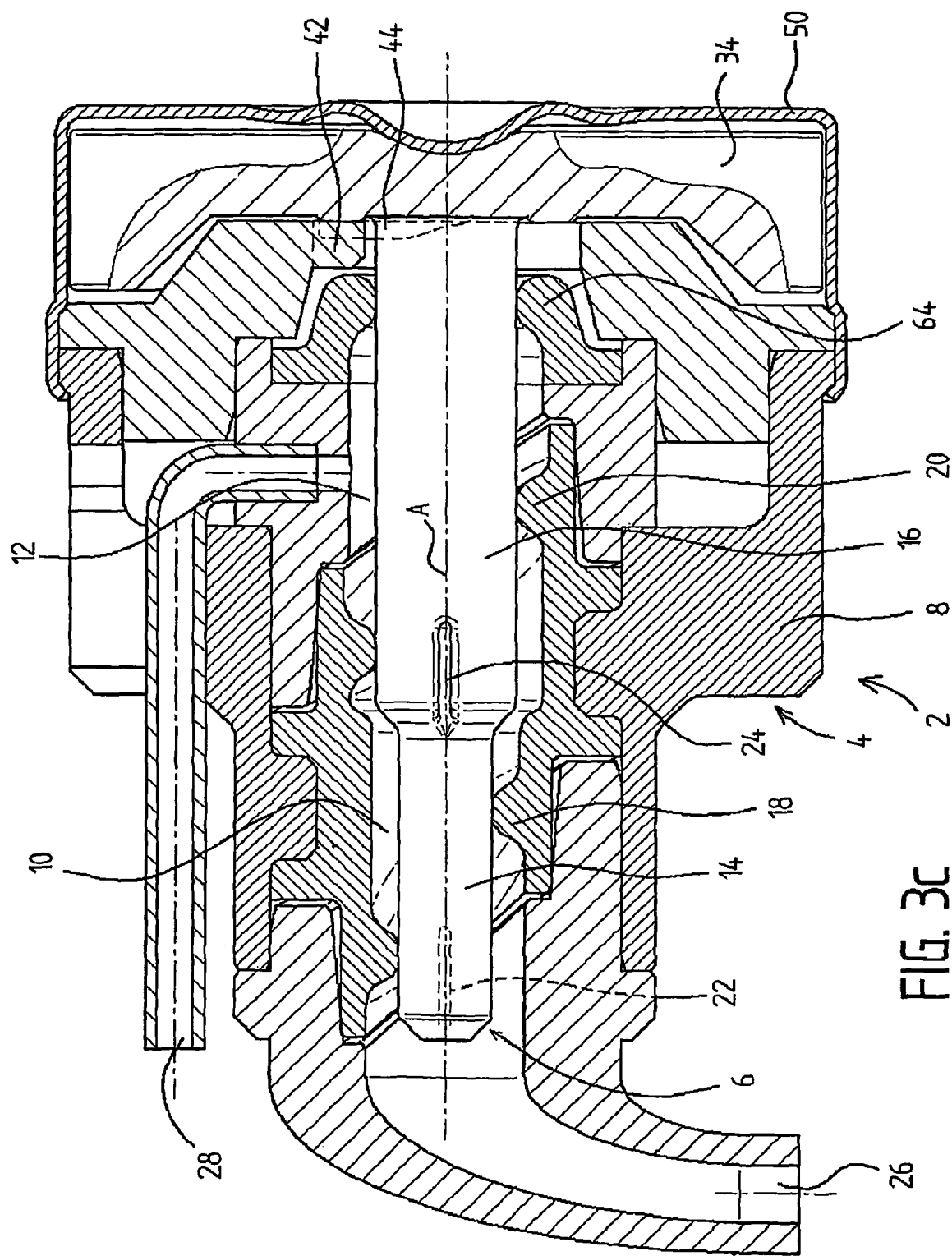
Figure 4:
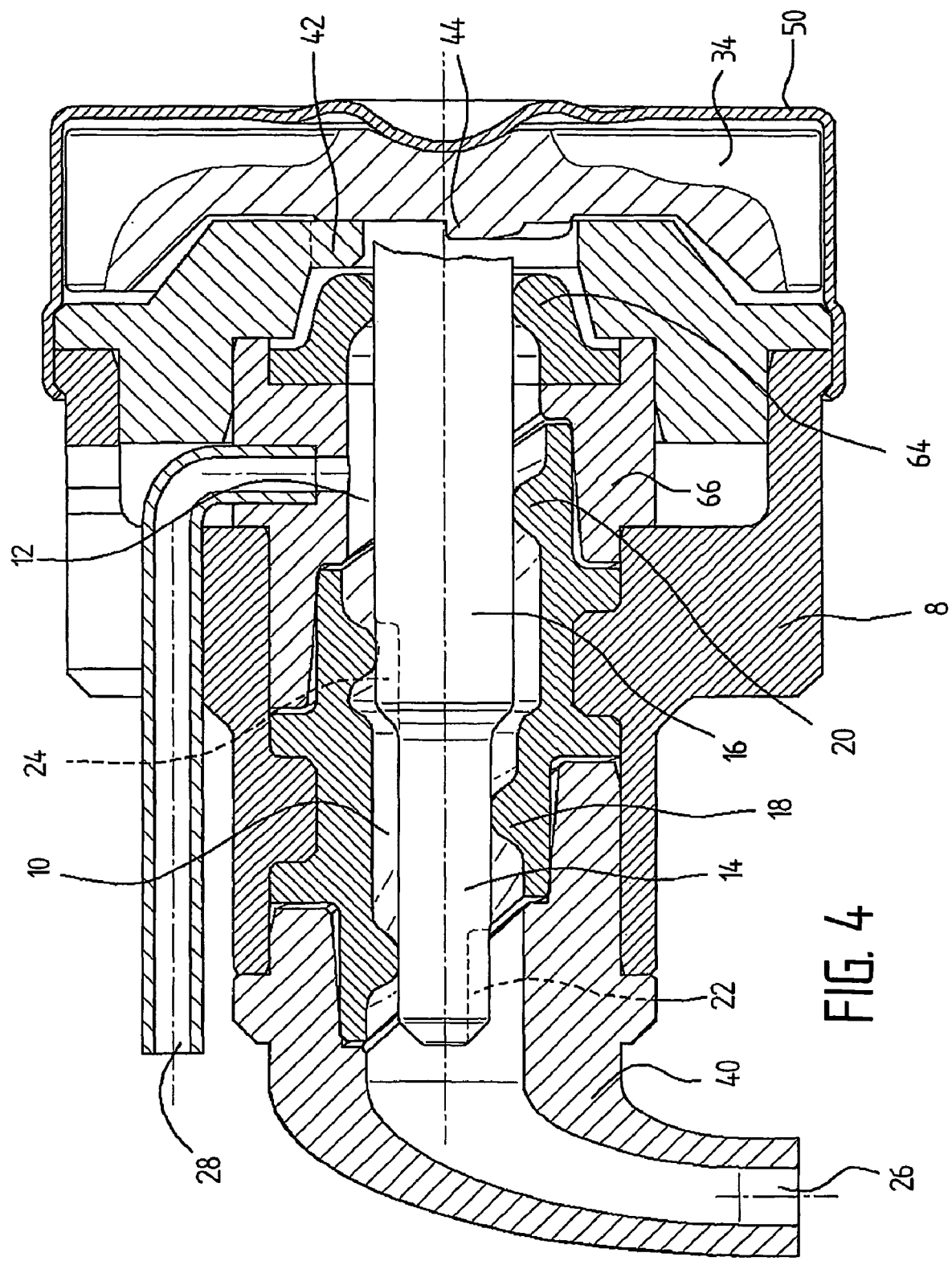
Figure 11A:
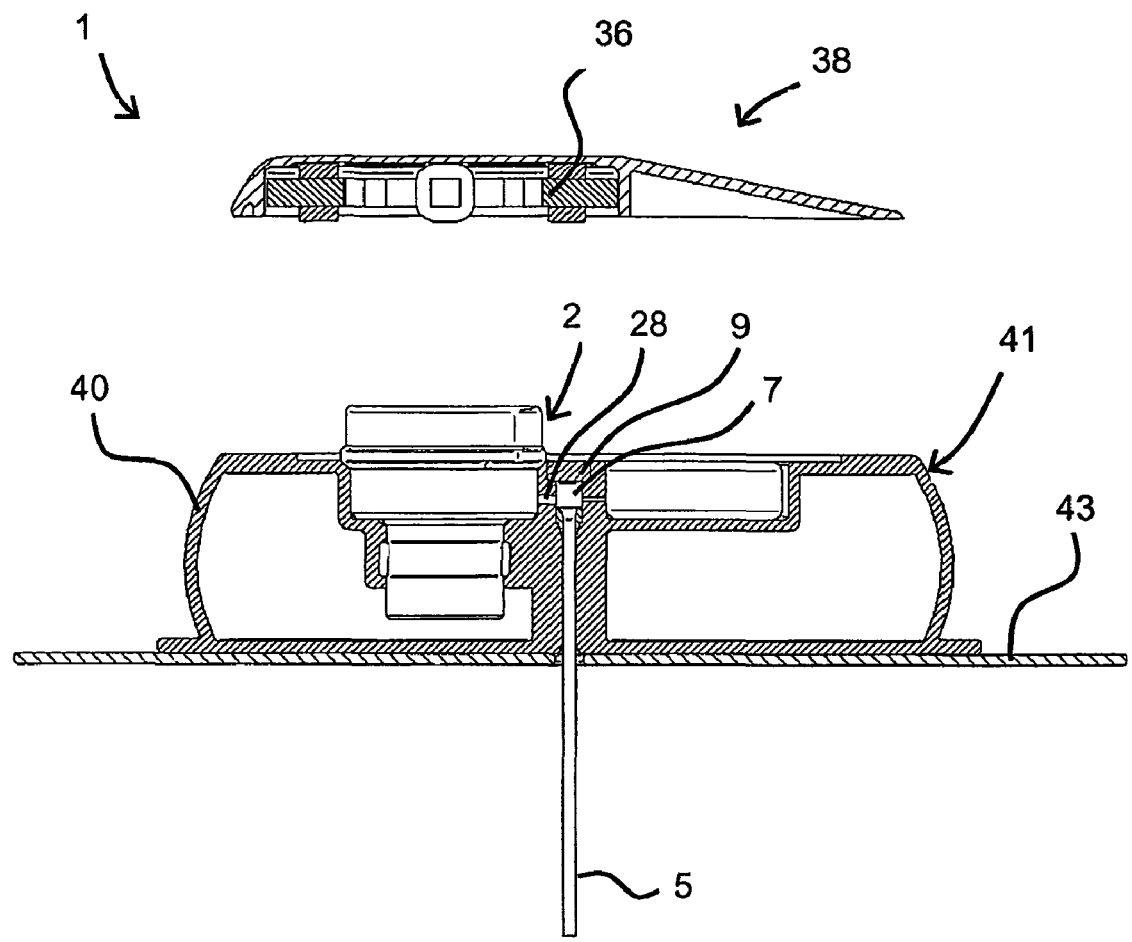
Figure 11B:
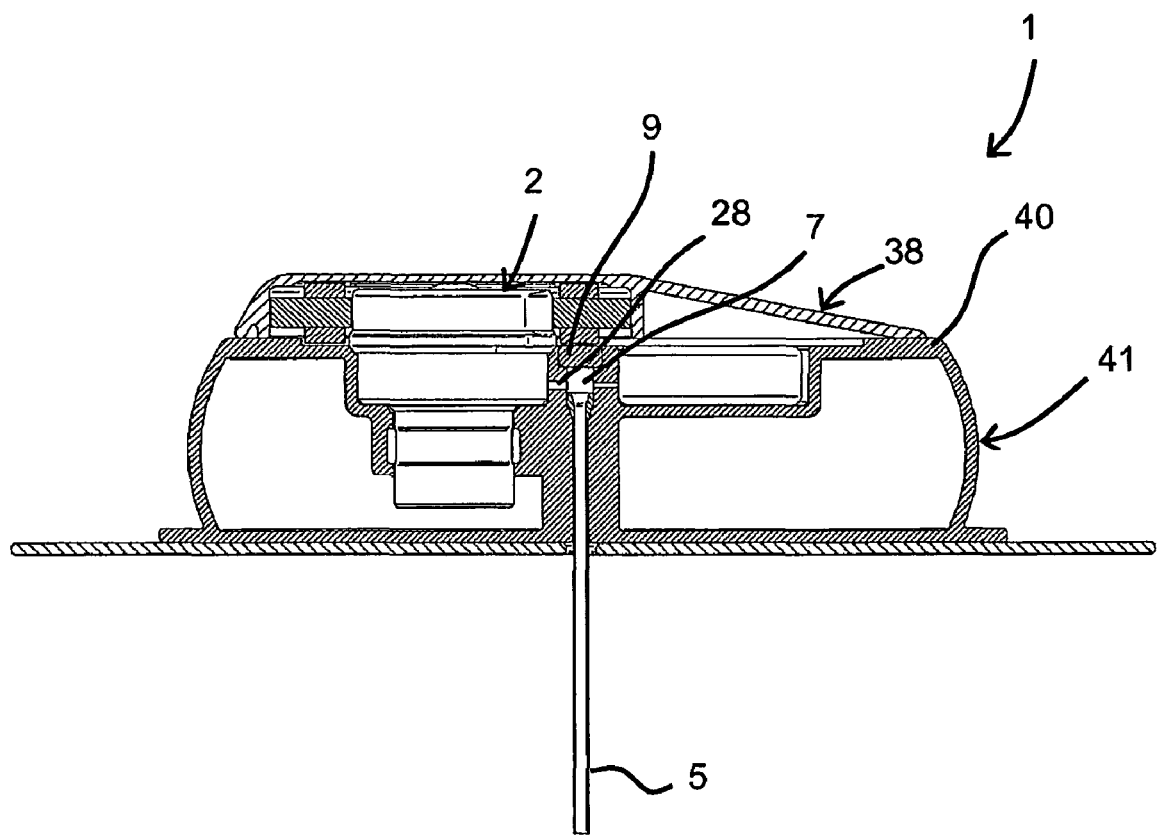
Figure 12A:
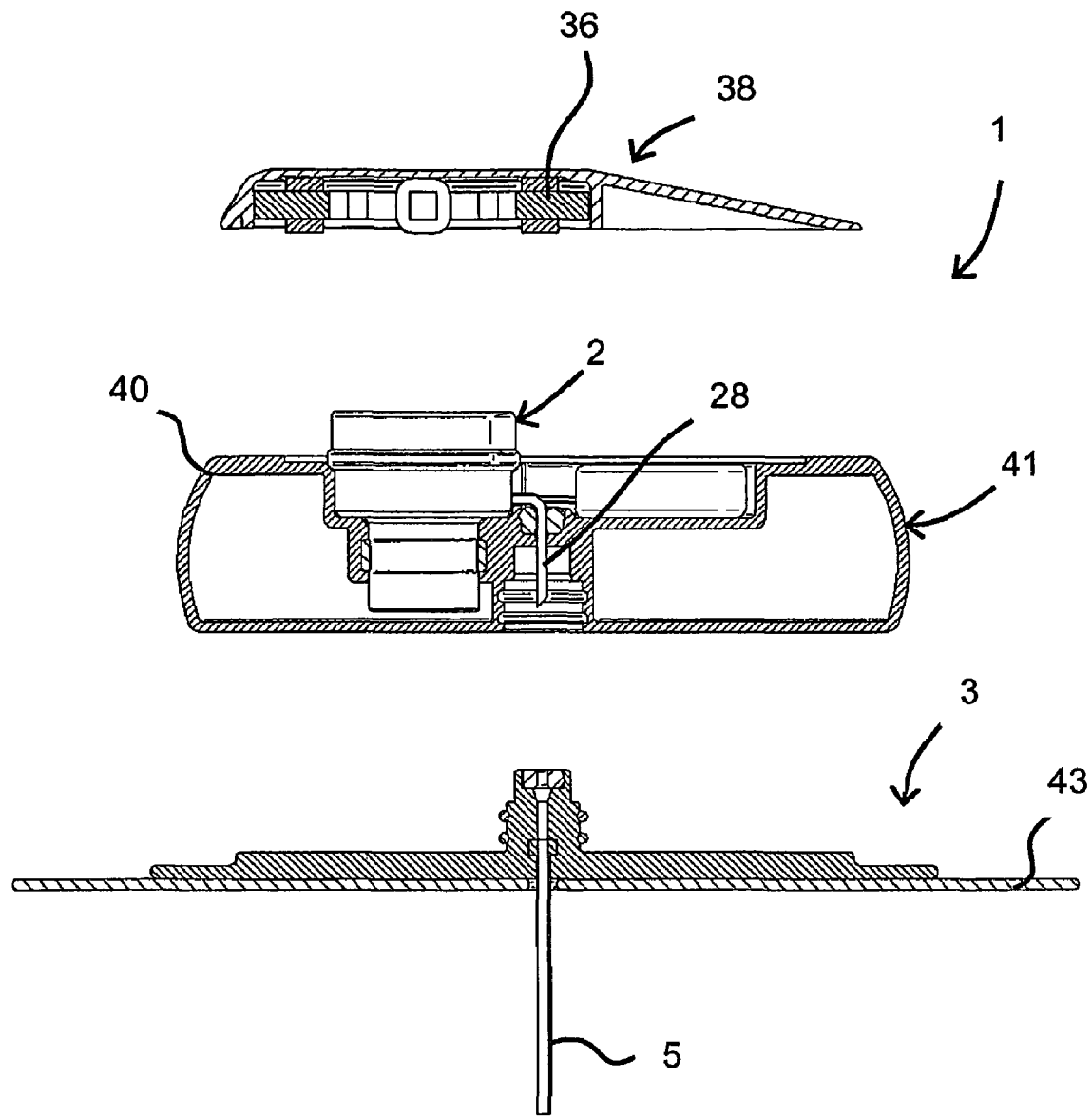
Figure 12B:
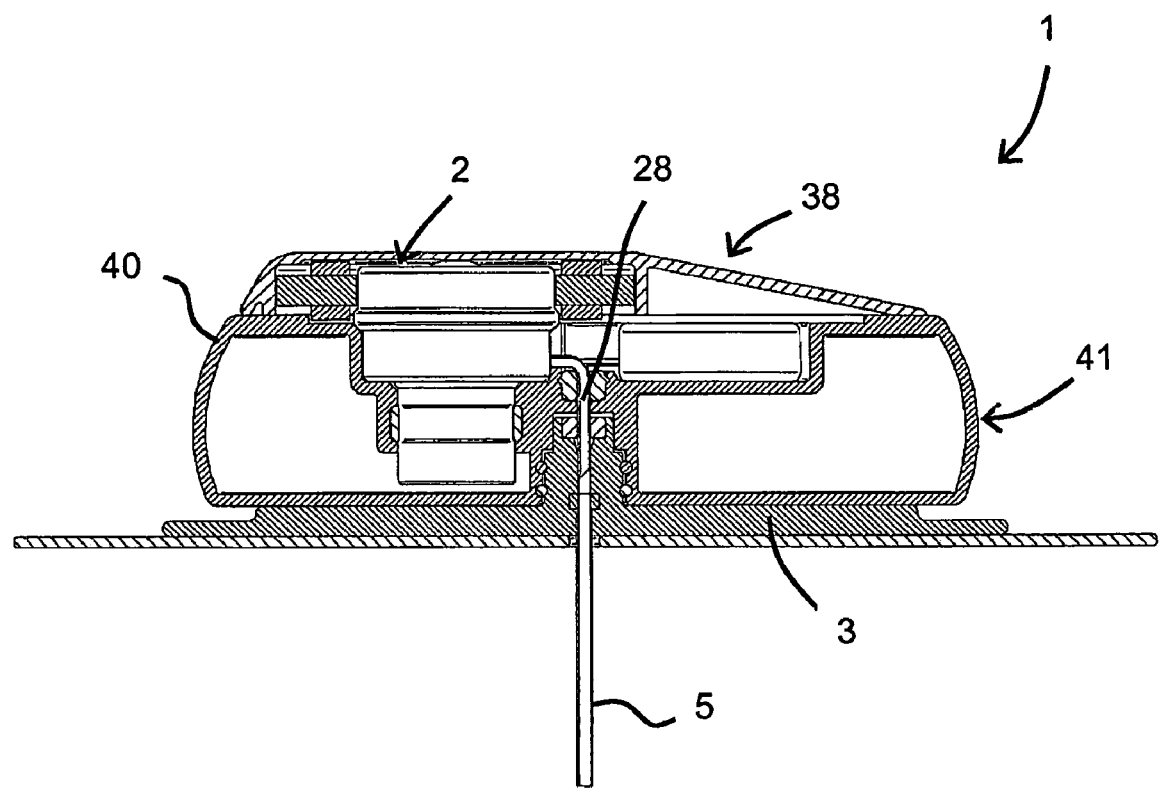

FIGS. 3a and 3b are similar to FIGS. 1a and 1b, respectively, except that the rotor is in an angular position of just past 180°;

FIG. 3c is a view similar to FIG. 3a, except that the rotor is in an axial position that is displaced with respect to the axial position shown in FIG. 3a;

FIG. 4 is similar to FIG. 1, except that the rotor is in an angular position of 270°;

FIG. 5 is an exploded perspective view of the rotor and corresponding stator part with cam element of the pump system according to a first embodiment of this invention;

FIGS. 6a to 6c are simplified schematic illustrations of the rotor with cam and complementary cam on the stator in different angular positions of the first embodiment;

FIG. 7 is an exploded perspective view of the rotor and corresponding stator part with cam element of the pump system according to a second embodiment of this invention;

FIGS. 8a and 8b are simplified schematic illustrations of the rotor with cam and complementary cam on the stator in different angular positions of the second embodiment;

FIG. 9a is a graphical explanatory schema of the opening and closing of seals as a function of the relative position of the rotor and stator cam elements of the first embodiment;

FIG. 9b is a graphical explanatory schema of the opening and closing of seals as a function of the relative position of the rotor and stator of the first embodiment, illustrating in particular the detection of an occlusion;

FIG. 9c is a graphical explanatory schema of the opening and closing of seals as a function of the relative position of the rotor and stator of the first embodiment, showing in particular the leakage or air detection function;

FIG. 10a is a graphical explanatory schema of the opening and closing of seals as a function of the relative position of the rotor and stator cam elements of the second embodiment;

FIG. 10b is a graphical explanatory schema of the opening and closing of seals as a function of the relative position of the rotor and stator of the second embodiment, illustrating in particular the detection of an occlusion;

FIG. 10c is a graphical explanatory schema of the opening and closing of seals as a function of the relative position of the rotor and stator of the second embodiment, showing in particular the leakage or air detection function;

FIG. 11a is an exploded cross-sectional view of a first embodiment of a patch pump incorporating a pump system according to this invention;

FIG. 11b is a cross-sectional view of the first embodiment of the patch pump;

FIG. 12a is an exploded cross-sectional view of a second embodiment of a patch pump incorporating a pump system according to this invention; and FIG. 12b is a cross-sectional view of the second embodiment of the patch pump.

Referring to the figures, in particular FIGS. 1a and 1b, an embodiment of a pump module according to this invention comprises a stator 4 and a rotor 6 rotatably mounted in the stator. The stator 4 comprises a housing 8 defining a chamber 10, 12, hereinafter called rotor chamber, within which first and second axial extensions 14, 16 of the rotor are mounted, and first and second seals 18, 20 mounted in the stator housing 8 and defining sealing rings sealingly surrounding the first and second axial extensions 14, 16 respectively of the rotor. Liquid supply channels 22, 24 are provided in the first and second axial extensions of the rotor. The first axial rotor extension has a generally cylindrical shape with a diameter D1 that is smaller than the diameter D2 of the second axial extension 16 which also has a generally cylindrical shape. The liquid supply channels 22, 24, that in the embodiment illustrated are in form of axially extending grooves on the surface of the respective extensions, allow inlet and outlet channels 26, 28 respectively to be in communication with a portion of the rotor chamber 10 situated between the first and second sealing rings 18, 20, depending on the angular and axial position of the rotor relative to the stator.

The first and second sealing rings 18, 20 are both inclined with respect to a plane perpendicular to the axis of rotation of the rotor whereby the angle of inclination of the sealing rings may be the same or may differ from each other. The main purpose of the inclined sealing rings, in conjunction with the liquid supply channels, is to act as valves that open and close as a function of the angular and axial position of the rotor. This enables pumping of liquid supplied from a reservoir through the inlet 26 and exited through the outlet 28, due to a change in volume in the rotor chamber portion 10 between the sealing rings 18, 20 caused by axial displacement of the rotor when either valve is open. The general functioning principle is described in prior patent application WO 2005 039674 which is incorporated herein by reference. In the preferred embodiment the inlet 26 is arranged at the axial centre of the rotor, however it is also possible to reverse the pumping direction by an appropriate change in the axial movement of the rotor as a function of the opening and closing of the valves such that the inlet 26 becomes an outlet and the outlet 28 becomes an inlet.

It may be noted that the opening and closing of liquid communication between the rotor chamber portion 10 and the inlet and outlet, may be achieved by different configurations in the design and the position of the liquid supply channels 22, 24 and seals 18, 20, their main purpose being to open and close liquid communication across the seals as a function of the angular and axial position of the rotor. For example, instead of grooves on the surface of the axial extensions, the liquid supply channels may be embedded within the rotor and have orifices (inlet, outlet) on the surface of the extension, whereby such orifices are not necessarily in axial alignment. Moreover, the liquid supply channels do not necessarily need to be on diametrally opposed positions on the rotor and the sealing rings could have a stepped or S-shape, in other words a non-constant angle of inclination.

In the embodiment shown, the sealings 18, 20 are formed as part of an integral sealing element 30 that is advantageously made by injection molding on a portion 32 of the housing, which may also be made by injection molding, for example in plastics material. The sealing rings could however also be separate elements, injection molded in the housing or assembled in the housing. The seals may for example be injected from silicon-based or thermoplastic elastomers or rubber whereby the molding of the housing part and seals provides a particularly cost-effective method for manufacturing components of the pump module, not only lowering the cost of manufacturing individual components but also the assembly thereof, while providing less components and improving precision of the assembled components.

The rotor 6 comprises a motor portion 34 that may for example generally be in the form of a cylindrical disc with one or more permanent magnets providing a plurality of magnetic poles therearound, driven in rotation by electromagnets 36 arranged in a base member 38.

The base member 38 may either be part of the pump 2, or part of a separate base unit into which the pump module is removably mounted. The base unit can be provided with electronics for controlling and operating the pump and/or for transmitting signals to a control unit via a wireless or wired link. Preferably, the pump module is removably inserted into the base unit such that the base unit may be re-used while the pump module is disposed off.

For example, referring to FIGS. 11a, 11b and 12a, 12b, a patch pump 1, 1' for application on the skin of a patient is shown, where the base member 38 comprising the electromagnets 36 for driving the rotor, is separably mounted to the pump module 2 and housing 40 of a reservoir 41 of the patch pump.

The pump unit or module 2 may advantageously be mounted to a reservoir containing the liquid to be pumped as a single unit that is disposed off once the liquid in the reservoir has been consumed or for other reasons such as after a certain period of use requiring a change of injection point. The pump housing 8 may be permanently mounted to a housing 40 integrated with or permanently fixed and sealed to the reservoir. Alternatively, the pump unit 2 could be separately provided from the liquid supply reservoir and connected thereto by any known sealed coupling means for example a needle piercing through a rubber membrane of a reservoir, a sealed bayonet coupling and other known means.

The incorporation of the pump and reservoir in a single unit is particularly advantageous in medical applications where a high degree of safety is required since it removes the risk of manipulations in connecting the pump to the liquid drug reservoir and prevents refilling of the reservoir and re-use of the pump, the unit being disposed of a single element.

Referring to FIGS. 11a, 11b and 12a, 12b, a particularly compact unit 1, 1' for example in the form of a patch pump can be provided, for connection to a separate patch unit 3 or incorporating a patch 3' with an adhesive base 43 that is mounted directly on the patient's skin for subcutaneous drug delivery.

The outlet 28 of the pump module 2 could be provided in the form of a suitable catheter adaptable for subcutaneous drug delivery, or could lead into a catheter 5, 5' of a patch pump or other system.

In the first patch pump embodiment (FIGS. 11a and 11b), the catheter 5, which could be in the form of a flexible or rigid tube, is introduced through the patients skin by means of a needle (not shown) positioned in the catheter 5 and cavity 7 of the patch pump housing 40 and protruding from a top of the patch pump. After application of the patch pump on the patient's skin and subcutaneous insertion of the needle and catheter, the needle is withdrawn and the cavity 7 is hermetically sealed by means of a self closing or self healing sealing plug 9.

In the second patch pump embodiment (FIGS. 12*a* and 12*b*), the patch 3 and catheter 5' are mounted on the patient, with the catheter being inserted subcutaneously by means of a needle (not shown), prior to mounting the reservoir 41 and pump module 2 on the patch unit 3.

The rotor magnetic poles and stator electromagnets may advantageously operate as a step motor that allows accurate angular stopping, starting and forward or reverse movement of the rotor. It would however also be possible to employ other motors and use the sensors for determining the angular position of the rotor relative to the stator.

The axial displacement of the rotor is defined by cam elements 42, 44 on the stator and rotor respectively. The cam elements have surfaces 46, 48 respectively that determine the axial position of the rotor relative to the stator as a function of the angular position of the rotor relative to the stator. In the embodiment shown, the cam element 44 is positioned on the generally disc shaped motor portion 34 of the rotor and extends over a certain arc. The cam surface 48 determines the axial position of the rotor, whereas the cam element 42 on the stator is a simple protrusion that runs along the rotor cam surface 48. It may be noted that the cam protrusion may take different shapes and it would also be possible to reverse the functions of the rotor and the stator cams, that is to have the protrusion on the rotor and the caming surface along which the protrusion runs on the stator.

The stator 4 is further provided with means for biasing the rotor in an axial direction relative to the stator such that the respective cam elements are pushed together. In the embodiment shown, the biasing means is in the form of a spring 50 that is fixed to the stator and that presses with a central portion 52 in the region of the rotational axis A of the rotor against an outer end of the rotor. The spring element 50 may have many different shapes and configurations, the main purpose being to bias the rotor cam element towards the cam element on the stator with a defined spring force. In the embodiment shown, the spring element is advantageously stamped and formed from a resilient sheet metal and mounted in the form of a clasp or cap over the rotor disc and having ends 54 clasped or fixed by other means to the stator housing. A spring beam portion 56 may be formed out of the cap portion 58 to press onto the rotor. The spring element 50 is preferably made of a non magnetic spring metal in order to allow the magnetic field between the rotor and stator to pass therethrough.

In order to reduce the axial length of the rotor and to improve its stability against tilting, the rotor body portion 34 may be provided with a central cavity portion 59 in which the cam elements are situated.

It is to be noted that within the scope of the invention, instead of a spring biasing the rotor, it would be possible to employ a magnetic force, generating means. In the latter embodiment, one could mount one or more permanent magnets within the rotor disc and oppose thereto one or more electromagnets or permanent magnets in the base 38 pushing the rotor towards the stator housing, or permanent magnets mounted within the stator housing 8 attracting the rotor. The axial position of the rotor may be detected by a position sensor that may for example comprise a permanent magnet 60 embedded in the rotor and a Hall sensor 62 in the base 38. A plurality of position sensors may be arranged around the circumference.

Advantageously, in the embodiment of the invention illustrated, the motor portion 34 of the rotor and the cam elements 42, 44 are not immersed in the liquid to be pumped, a third seal 64 being positioned around the axial extension 16 proximate the motor portion 34. The third seal 64 reduces the volume in the outlet portion 12 of the rotor chamber and prevents a backflow step which occurs in the prior art pump described in WO 2005 039674. The arrangement of the third seal 64 on the second axial extension 16 has a number of advantages: it reduces the volume in the rotor chamber and improves elimination of air pockets in the rotor chamber during the start cycle; it ensures forward flow pumping only; and it provides a further bearing support improving stability against tilting of the rotor.

The third seal 64 may advantageously be injection molded from an elastomer, such as a silicone based or thermoplastic elastomer or rubber, with an injection molded housing part 66, assembled to or integral with the housing part 32. A further advantage of having the rotor motor portion and cam elements in air, rather than immersed in the liquid to be pumped, is a reduction of shear forces on the liquid, thus reducing possible adverse consequences, for example large molecules such as insulin may easily degrade under the influence of shear forces.

Referring in particular to FIGS. 5, 6*a* to 6*c* and 9 concerning a first cam variant and FIGS. 7, 8*a*, 8*b* and 10 concerning a second cam variant, the functioning of the pump and security features of will be described in more detail.

Figure 9:
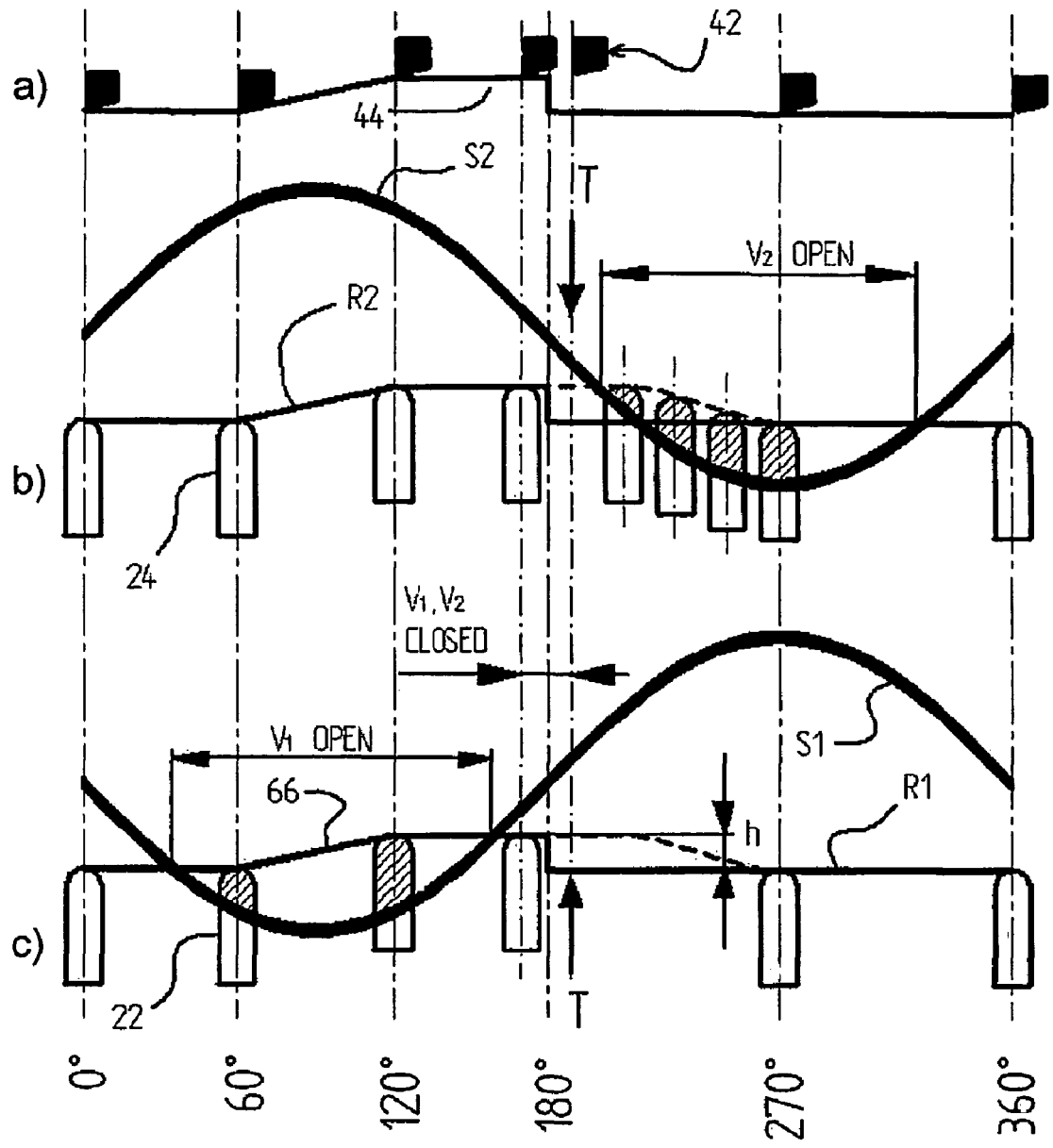
Figure 10:
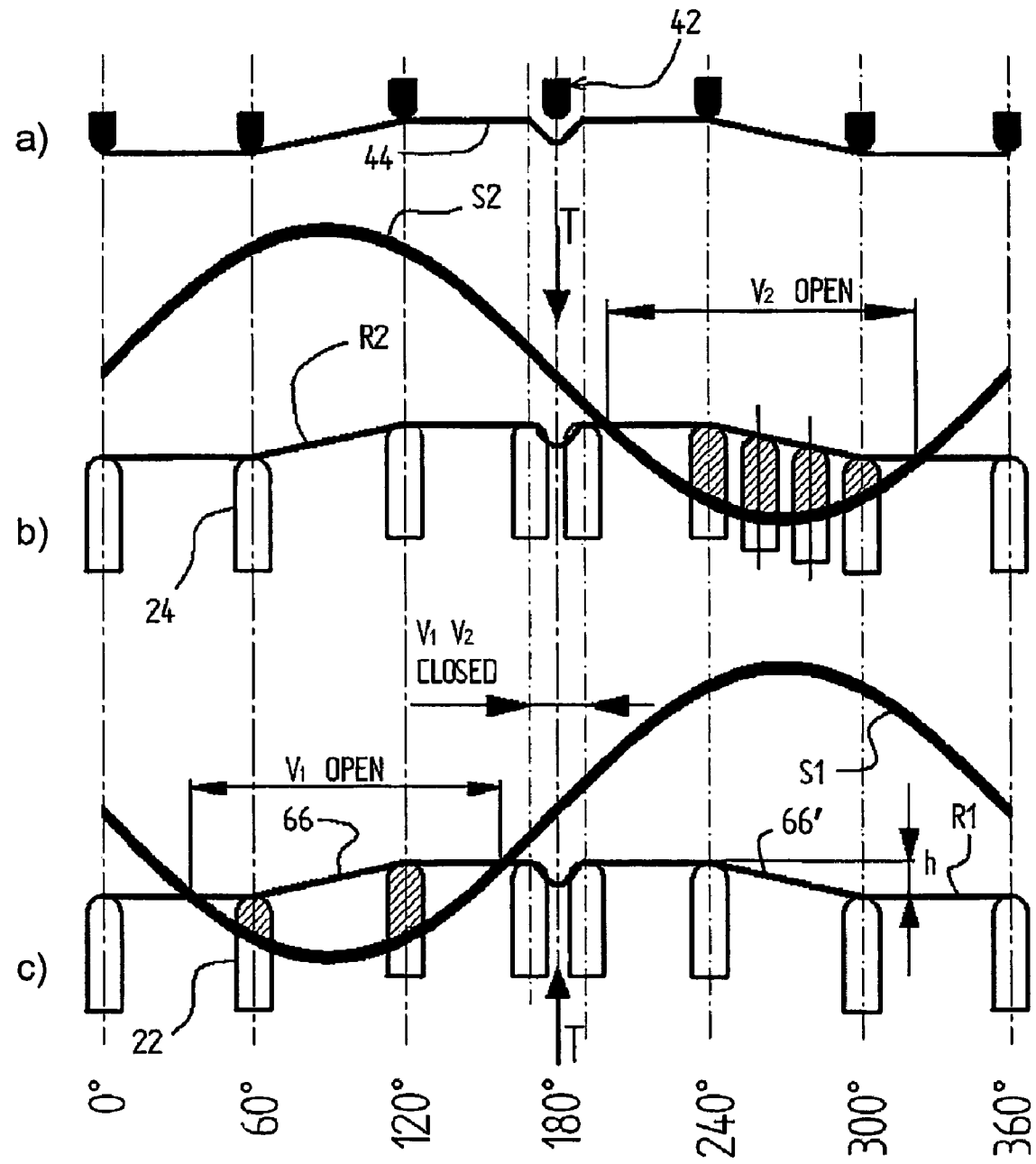

In FIGS. 9 and 10, line S1 represents the relative axial position of the first liquid supply channel 22 with respect to the first seal 18 as a function of the angular position of the rotor and the line S2 represents the relative axial position of the second liquid supply channel 24 with respect to the second seal 20 as a function of the angular position of the rotor. Lines R1 and R2 represent respectively the axial position (i.e. displacement) of the rotor as a function of the angular position, as defined by the cam surface 48. Superposition of the lines S1 and R1 show the positions in which the first valve V1 is open and closed, and superposition of the lines S2 and R2 show the angular position over which the second valve V2 is open and closed. One can also tell from the two graphs the overlapping positions where both the first and second valves V1, V2 are closed whereby both valves are never open at the same time in order to avoid direct liquid communication between the reservoir and the outlet. In these graphs, the positions of the liquid supply channels 22, 24 and the cam elements 42, 44 are schematically illustrated.

At the position 0° as illustrated in FIG. 7, which corresponds to the position of the rotor as illustrated in FIGS. 1*a* and 1*b*, the relative position of the liquid supply channels 22, 24 and the first and second seals 18, 20 respectively is such that there is no liquid communication across either seals. In other words, the first and second valves are closed. As the rotor rotates, between an angular position of approximately 40° and 170° an end of the first liquid supply channel 22 crosses over the first seal 18 allowing liquid communication between the inlet 26 to the reservoir and the rotor chamber portion 10 between the seals. In other words, the first valve V1 is open. Over this angular position where the first valve is open, the cam surface 48 has a ramp 66 such that the rotor is displaced against the biasing force of the spring F. As the axial extension is moving in direction F (as shown in FIG. 1*a*), the volume of the rotor chamber portion 10 between the first and second seals 18, 20 increases thereby drawing liquid from the reservoir into this chamber portion.

At around an angular position of 170° the first valve V1 then closes and remains closed for the rest of the 360° cycle illustrated. The second valve V2, defined by cooperation of the second liquid supply channel 24 and the second seal 20, opens as can be seen in FIG. 7 at approximately 200° until approximately 330°.

There is thus an overlap from approximately 170° to 200° where both valves are closed, thus providing a safety margin ensuring that both valves are never open simultaneously. Whilst both valves are closed and functioning properly, the axial position of the rotor is blocked due to the incompressibility of the fluid in the rotor chamber portion 10.

Once the second valve 24, 20 opens, the biasing force on the rotor reverses the axial direction of the rotor F thus reducing the volume in the chamber portion 10 such that liquid therein is pumped into the rotor chamber outlet portion 12 and thus towards the pump outlet 28.

The cam elements are designed such that, at least over a portion of the angular displacement when both valves are closed, the cam elements are separated axially by a certain maximum distance h (see FIGS. 6b, 9 and 8b, 10). In the first variant shown in FIG. 9, this axial separation between the cam elements is achieved at approximately 190° and in the second variant shown in FIG. 10, at approximately 180°, whereby both valves are still closed and the axial position of the rotor should be blocked. The rotor can be stopped at this position (hereinafter called "test position" T), which may be determined by the position sensor, or by use of the step motor determining a certain position, for purposes of determining any malfunctioning of the valves or the presence of air within the rotor chamber portion 10.

When the rotor is at the test position T, if either of the valves leak due to a faulty or damaged seal or for any other reason, liquid in the chamber portion 10 between the first and second seals will leak out through the faulty valve in view of the biasing force exerted on the rotor by the spring. Even in the situation where the valves function correctly and do not leak, if there is any air within the rotor chamber portion 10 the compressibility thereof will allow some axial movement of the rotor. Axial displacement of the rotor can be detected by a position sensor for example the position sensor 60, 62 comprising a magnet on the rotor and a Hall Effect sensor on the base or in the stator. The sensor could measure an absolute value of the axial distance, but preferably would output a differential measurement of axial distance of the rotor relative to the stator such that an axial displacement would be detected rather than the absolute position of the rotor relative to the stator. The latter eliminates any problems related to manufacturing tolerances and sensor measurement drift.

In the case of an axial displacement of the rotor in the test position T, the position sensor would generate an alarm. The alarm could for example cause the pump system to go through a specified number of pumping cycles to ensure removal of any air in the pump, followed by a second test whereby in event of axial displacement of the rotor at the test position T the control unit would indicate a malfunctioning of the pump.

The axial distance h separating the cam elements may also be used to test for pump blockage that may be due either to the pump or due to a clot or other blockage in the catheter downstream of the pump. If such a blockage occurs, the biasing force on the rotor will not be able to push the cam elements together once the second valve V2 opens whereby the differential measure of axial position of the rotor relative to the stator will detect that no change in axial position of the rotor has occurred as is expected once the second valve opens. In other words, the reading of both the angular position of the rotor and the axial position will allow detection of a blockage in the pump or downstream of the pump which would signal a malfunction.

The aforedescribed configuration of the cam elements 42, 44 may also be advantageously used to set a reference position of the rotor that may be used to initialize the counting of the step motor, and based thereon, to rotate the rotor a specified angle. The reference position will thus enable precise and reliable angular positioning of the rotor which would be useful in particular for stopping the rotor at the test position T when performing the test procedure.

In the first variant (shown in FIGS. 5, 6a-6c, 9) the reference position may be defined by a shoulder 68 on the cam element 44 on the rotor abutting against a corresponding shoulder 70 on the stator cam element 42. To attain the reference position, the rotor is rotated a specified number of cycles depending whether the pump is in an initial start-up phase where the pump system is filled with liquid and air removed or in an intermediate phase, stopped in a position where the axial distance between the cam element on the stator 42 and rotor become substantially null (which can be detected by the axial position sensor by differential measurement or otherwise as described above) and then reversed as illustrated in FIG. 6c until the shoulders 68, 70 abut and prevent further reverse rotation. This abutting position can then be stored in the control unit as a reference position of the rotor.

In the second variant (shown in FIGS. 7, 8a, 8b, 9), the reference position may be set by detecting the axial displacement profile of the rotor when the cam 42 engages the camming surface, as a function of the rotor angular displacement. The second variant has a reverse ramp 66' in lieu of the shoulder of the first variant, to allow reverse rotation of the rotor for reverse pump action of the system. In other terms, in the second variant, the pump can pump liquids either way, which may be desired in certain applications.

What is claimed is:

1. A pump comprising a stator, a rotor comprising an axial extension slidably and rotatably mounted at least partially in a rotor chamber of the stator, and at least a first valve between an inlet and the rotor chamber, and at least a second valve between the rotor chamber and an outlet, wherein both the first valve and the second valve open and close as a function of at least an angular displacement of the rotor, the pump further comprising interacting rotor cam element and stator cam element on the rotor and stator respectively, and biasing means acting on the rotor for applying a force on the rotor in an axial direction of the stator cam element, said rotor cam element and stator cam element being configured such that they are separated by a certain axial distance h at a specified angular position of the rotor in respect to the stator when both valves are closed and at said specified angular position said rotor cam element is not in contact with said stator cam element.

2. The pump according to claim 1, wherein the rotor comprises at least first and second axial extensions having different diameters, and first and second seals mounted around the first and second axial extensions, the axial extensions being provided with liquid supply channels cooperating with the respective first and second seals to create the first and second valves that open and close liquid communication across the respective seal as a function of said at least an angular displacement of the rotor.

3. The pump according to claim 2, wherein the cam elements comprise abutment shoulders engageable upon reverse rotation of the rotor in order to define an angular reference position of the rotor relative to the stator.

4. The pump according to claim 1, wherein the cam element provided around the stator is in the form of a protrusion and the cam element on the rotor is provided on a motor portion from which the axial extensions extend, the rotor cam element comprising a camming surface extending along an arc and of varying axial height as a function of an angular position of the arc.

5. The pump according to claim 1, wherein the biasing means comprises a spring attached to the stator, pressing on the rotor.

6. The pump according to claim 1, wherein the inlet of the pump is situated at an end of a first axial rotor extension.

7. The pump according to claim 6, wherein a housing portion defining the pump inlet is integrally formed with a reservoir for containing a liquid to be pumped.

8. The pump according to claim 2, wherein the first and second seals are formed as a single integral sealing element.

9. The pump according to claim 2, further comprising a third seal mounted around the second axial extension proximate a motor portion of the rotor, delimiting an outlet portion of the rotor chamber.

10. The pump according to claim 2, wherein the seals are injection molded with at least a housing part of a stator housing.

11. A pump comprising a rotor comprising a motor portion, first and second axial extensions having different diameters extending therefrom, a stator comprising a stator housing having a rotor chamber for receiving at least the axial extensions therein, and first and second seals mounted around the first and second axial extensions, the axial extensions being provided with liquid supply channels cooperating with the respective first and second seals to create first and second valves that open and close liquid communication across the respective seal as a function of at least an angular displacement of the rotor, wherein the pump comprises a third seal mounted around the second axial extension proximate a motor portion of the rotor, delimiting an outlet portion of the rotor chamber.

12. The pump according to claim 11, comprising interacting rotor cam element on the rotor and stator cam element on the stator, and biasing means acting on the rotor for applying a force on the rotor in an axial direction of the stator cam element, said rotor cam element and stator cam element being configured such that they are separated by a certain axial distance h at a specified angular position when both valves are closed.

13. The pump according to claim 12, wherein the cam elements comprise abutment shoulders engageable upon reverse rotation of the rotor in order to define an angular reference position of the rotor relative to the stator.

14. The pump according to claim 12, wherein the stator cam element is in the form of a protrusion and the rotor cam element is provided on the motor portion from which the axial extensions extend, the rotor cam element comprising a camming surface extending along an arc and of varying axial height as a function of an angular position of the arc.

15. The pump according to claim 12, wherein the biasing means comprises a spring attached to the stator, pressing on the rotor.

16. The pump according to claim 11, wherein an inlet of the pump is situated at an end of the first axial extension of the rotor.

17. The pump according to claim 16, wherein a housing portion defining a pump inlet is integrally formed with a reservoir for containing the liquid to be pumped.

18. The pump according to claim 11, wherein the first and second seals are formed as a single integral sealing element.

19. The pump according to claim 11, wherein the seals are injection molded with at least a part of the stator housing.

20. A patch pump device comprising a disposable unit including a reservoir and a pump mounted to the reservoir, said pump comprising a stator, a rotor comprising an axial extension slidably and rotatably mounted at least partially in a rotor chamber of the stator, and at least a first valve between an inlet and the rotor chamber, and at least a second valve between the rotor chamber and an outlet, wherein both the first valve and the second valve open and close as a function of at least an angular displacement of the rotor, the pump further comprising interacting rotor cam element and stator cam element on the rotor and stator respectively, and biasing means acting on the rotor for applying a force on the rotor in an axial direction of the stator cam element, said rotor cam element and stator cam element being configured such that they are separated by a certain axial distance h at a specified angular position of the rotor in respect to the stator when both valves are closed and at said specified angular position said rotor cam element is not in contact with said stator cam element.

21. The patch pump device according to claim 20, further comprising an adhesive base adapted for adhesive mounting of the patch pump on a patient's skin.

22. The patch pump device according to claim 20, further comprising a catheter in communication with an outlet of the pump and adapted for subcutaneous drug administration.

23. The patch pump device according to claim 20, further comprising a reusable base unit comprising a drive for driving the pump rotor, the base unit being removably mounted to the disposable unit.

24. A patch pump device comprising a disposable unit including a reservoir and a pump mounted to the reservoir, said pump comprising a rotor comprising a motor portion, first and second axial extensions having different diameters extending therefrom, a stator comprising a stator housing having a rotor chamber for receiving at least the axial extensions therein, and first and second seals mounted around the first and second axial extensions, the axial extensions being provided with liquid supply channels cooperating with the respective first and second seals to create first and second valves that open and close liquid communication across the respective seal as a function of at least an angular displacement of the rotor, wherein the pump comprises a third seal mounted around the second axial extension proximate a motor portion of the rotor, delimiting an outlet portion of the rotor chamber.

25. The patch pump device according to claim 24, further comprising an adhesive base adapted for adhesive mounting of the patch pump on a patient's skin.

26. The patch pump device according to claim 24, further comprising a catheter in communication with an outlet of the pump and adapted for subcutaneous drug administration.

27. The patch pump device according to claim 24, further comprising a reusable base unit comprising a drive for driving the pump rotor, the base unit being removably mounted to the disposable unit.

28. A method of operating a pump including a stator, a rotor comprising an axial extension slidably and rotatably mounted at least partially in a rotor chamber of the stator, and at least first and second valves between an inlet and the rotor chamber, respectively between the rotor chamber and an outlet, wherein both the first valve and the second valve open and close as a function of at least an angular position of the rotor, the method including:
  detecting axial displacement of the rotor as a function of the angular position of the rotor; and
  comparing the axial displacement detected with an expected displacement value in order to determine if there is a malfunction due to blockage downstream, leakage of a valve, or air in the rotor chamber.

29. The method according to claim 28, including a step of testing a malfunction due to air in the rotor chamber or leakage of either valve by:
turning the rotor to a test position where the first and second valves are closed; and
applying a force on the rotor in an axial direction.

30. The method according to claim 29, the pump further comprising interacting rotor cam element on the rotor and stator cam element on the stator, and biasing means acting on the rotor for applying a force on the rotor in an axial direction of the stator cam element, the method including:
selecting as the test position a position where the rotor cam element and stator cam element are separated by a certain axial distance h and both valves are closed.

31. The method according to claim 28, including a step of defining a reference angular position of the rotor relative to the stator by:
turning the rotor one or more cycles in a pumping direction; and
subsequently reversing the rotor rotation until shoulders of the rotor and stator cam elements abut, and prevent further reverse rotation.

32. A method of operating a pump including a stator, a rotor comprising an axial extension slidably and rotatably mounted at least partially in a rotor chamber of the stator, and at least a first valve between an inlet and the rotor chamber, and a second valve between the rotor chamber and an outlet, wherein both the first valve and the second valve open and close as a function of at least an angular displacement of the rotor, the pump further comprising interacting rotor cam element on the rotor and stator cam element on the stator and biasing means acting on the rotor for applying a force on the rotor in the axial direction of the stator cam elements, the method including:
turning the rotor one or more cycles in a pumping direction; and
subsequently reversing the rotor rotation until a shoulder of the rotor cam element and a shoulder of the stator cam element abut in order to define a reference angular position of the rotor relative to the stator.

33. A pump including a stator, a rotor comprising an axial extension slidably and rotatably mounted at least partially in a rotor chamber of the stator, and at least a first valve between an inlet and the rotor chamber, and at least a second valve between the rotor chamber and an outlet, wherein both the first valve and the second valve open and close as a function of at least an angular displacement of the rotor, the pump further comprising interacting rotor cam element on the rotor and stator cam element on the stator, and biasing means acting on the rotor for applying a force on the rotor in an axial direction of the stator cam element, said rotor cam element and stator cam element being configured such that they are separated by a certain axial distance h at a specified angular position of the rotor in respect to the stator when both valves are closed, wherein the rotor comprises at least first and second axial extensions having different diameters, and first and second seals mounted around the first and second axial extensions, the axial extensions being provided with liquid supply channels cooperating with the respective first and second seals to create first and second valves that open and close liquid communication across the respective seal as a function of at least the angular displacement of the rotor.

34. The pump according to claim 33, wherein the cam elements comprise abutment shoulders engageable upon reverse rotation of the rotor in order to define an angular reference position of the rotor relative to the stator.

35. The pump according to claim 33, wherein the first and second seals are formed as a single integral sealing element.

36. The pump according to claim 33, further comprising a third seal mounted around the second axial extension proximate the motor portion of the rotor, delimiting an outlet portion of the rotor chamber.

37. The pump according to claim 33, wherein the seals are injection molded with at least a housing part of a stator housing.

* * * * *

UNITED STATES PATENT AND TRADEMARK OFFICE
CERTIFICATE OF CORRECTION

PATENT NO. : 8,282,366 B2  
APPLICATION NO. : 12/086661  
DATED : October 9, 2012  
INVENTOR(S) : Josef Hilber and Sigfrid Straessler Page 1 of 1

It is certified that error appears in the above-identified patent and that said Letters Patent is hereby corrected as shown below:

<u>Column 11,</u>
Lines 21-22, "of a stator housing." should read --of the stator.--.

<u>Column 14,</u>
Lines 36-37, "of a stator housing." should read --of the stator.--.

Signed and Sealed this
Twelfth Day of February, 2013

Teresa Stanek Rea
*Acting Director of the United States Patent and Trademark Office*